(12) United States Patent
Hu et al.

(10) Patent No.: US 8,154,728 B2
(45) Date of Patent: Apr. 10, 2012

(54) ANALYTICAL EQUIPMENT ENCLOSURE INCORPORATING PHASE CHANGING MATERIALS

(75) Inventors: Xuejiao Hu, Rancho Cucamonga, CA (US); Alfred Feitisch, Los Gatos, CA (US)

(73) Assignee: SpectraSensors, Inc., Rancho Cucamonga, CA (US)

( * ) Notice: Subject to any disclaimer, the term of this patent is extended or adjusted under 35 U.S.C. 154(b) by 645 days.

(21) Appl. No.: 12/347,368

(22) Filed: Dec. 31, 2008

(65) Prior Publication Data

US 2010/0169027 A1 Jul. 1, 2010

(51) Int. Cl.
*G01N 21/00* (2006.01)
*H01S 3/04* (2006.01)

(52) U.S. Cl. ............. 356/437; 356/440; 372/34; 372/36
(58) Field of Classification Search ........... 356/432–444
See application file for complete search history.

(56) References Cited

U.S. PATENT DOCUMENTS

| | | | | |
|---|---|---|---|---|
| 3,554,275 A | * | 1/1971 | Schade, Jr. ................... | 165/156 |
| 4,219,072 A | * | 8/1980 | Barlow, Sr. ................... | 165/276 |
| 5,220,954 A | * | 6/1993 | Longardner et al. ........... | 165/10 |
| 5,331,409 A | * | 7/1994 | Thurtell et al. ............... | 356/437 |
| 5,696,783 A | * | 12/1997 | Montgomery .................. | 372/35 |
| 5,945,217 A | * | 8/1999 | Hanrahan ...................... | 428/389 |
| 6,307,871 B1 | * | 10/2001 | Heberle ......................... | 372/34 |
| 6,351,478 B1 | * | 2/2002 | Heberle ......................... | 372/36 |
| 7,458,201 B2 | * | 12/2008 | Brady ........................... | 60/200.1 |
| 7,707,841 B2 | * | 5/2010 | Turner, Jr. ...................... | 62/121 |
| 8,015,856 B2 | * | 9/2011 | Hadley et al. ................. | 73/23.35 |
| 2004/0069454 A1 | * | 4/2004 | Bonsignore et al. ...... | 165/104.15 |

FOREIGN PATENT DOCUMENTS

| | | |
|---|---|---|
| JP | 04-163298 A | 6/1992 |
| JP | 2008-107091 A | 5/2008 |
| KR | 20040095560 A | 11/2004 |

* cited by examiner

*Primary Examiner* — Gregory J Toatley
*Assistant Examiner* — Jarreas C Underwood
(74) *Attorney, Agent, or Firm* — Mintz, Levin, Cohn, Ferris, Glovsky and Popeo, P.C.

(57) ABSTRACT

Thermally controlled enclosures that can be used with gas analyzers are described. The enclosures incorporate one or more phase changing materials that buffer ambient and internal heat loads to reduce the power consumption demand of mechanical or electronic heating apparatus. Maintenance of gas analyzer equipment at a consistent temperature can be important to achieving stable and reproducible results. Related systems, apparatus, methods, and/or articles are also described.

21 Claims, 6 Drawing Sheets

ANALYTICAL EQUIPMENT ENCLOSURE INCORPORATING PHASE CHANGING MATERIALS

FIELD

The subject matter described herein relates to enclosures that can be used with analytical equipment, including but not limited to gas analyzers such as those based on tunable diode laser spectroscopy.

BACKGROUND

Gas analyzers, such as for example those that employ tunable diode laser spectroscopy, typically require mounting of a laser source on a heat sink or a thermo electric cooler (TEC) to achieve and maintain the required lasing frequency for a chosen trace gas analysis. A thermistor and an electronic feedback control loop are typically used to stabilize laser temperature to the required accuracy levels. However, laser temperature stability can be influenced by ambient temperature conditions, especially by changing ambient temperature conditions. Changing temperature conditions can in some instances exceed the ability of the control circuit to maintain laser temperature and frequency at the required levels. If this cannot be achieved, the laser may shift away from its pre-set frequency, thereby generating unacceptable measurement errors.

Currently available TDL-based gas analyzers typically employ an insulated enclosure coupled to a heater to maintain the enclosure temperature at a relatively constant value that is elevated relative to typically encountered ambient conditions. These heated enclosures can require substantial energy consumption. In addition, if the gas analyzer is installed in a location where it might be exposed to hazardous and/or flammable compounds, additional costs can be added by the requirement of using a hazardous location approved heater and thermostat. At rural installations, electricity supplies can be limited, and provision of 200 or more watts to run a heater enclosure device can be problematic. Use of TDL-based gas analyzers with natural gas pipelines is increasing. Such pipelines typically run long distances over which easy access to AC power is limited or non-existent. Solar panels or thermo electric generators can be used. However, it can be difficult to supply more than 50 W power at acceptable cost levels with these generation sources.

SUMMARY

In one aspect, an apparatus includes an enclosure having an outer shell that is resistant to and compatible with an operating environment, one or more gas analyzer components disposed within the outer shell, and a mass of a phase changing material disposed within the outer shell. The phase changing material has a phase transition temperature at which the phase changing material transitions from a first phase to a second phase while absorbing or releasing a latent heat energy $\Delta H_L$. This phase transition temperature is within a desired operating temperature range of the one or more gas analyzer components. The mass M of the phase changing material is given by the equation $$M \geq \frac{F_T}{\Delta H_L} \quad (1)$$

where $F_T$ is an expected net heat energy flux from the operating environment into the enclosure during a period of an operating day during which an ambient temperature outside of the enclosure exceeds the phase transition temperature.

In an interrelated aspect, a method includes receiving a gas sample in a sample cell of a gas analyzer, projecting light produced by a laser light source through the gas sample in the sample cell and onto a detector, quantifying an intensity of the light received at the detector, and calculating a concentration of at least one target analyte in the gas sample based on the intensity. The temperature of the laser light source is controlled to within an operating temperature range by operating the light source inside of an enclosure that includes an outer shell resistant to and compatible with an operating environment. Also contained within the outer shell is a mass of a phase changing material that has a phase transition temperature at which the phase changing material transitions from a first phase to a second phase while absorbing or releasing a latent heat energy $\Delta H_L$. This phase transition temperature is within the operating temperature range. The mass M of the phase changing material is given by equation 1.

In another interrelated aspect, a method includes selecting a phase changing material having a phase transition temperature at which the phase changing material transitions from a first phase to a second phase while absorbing or releasing a latent heat energy $\Delta H_L$. The phase transition temperature is within an operating temperature range of one or more gas analyzer components. The method also includes calculating a necessary mass M of the phase changing material necessary to maintain the one or more gas analyzer components within the operating temperature range using equation 1, assembling the enclosure such that the enclosure includes an inner enclosure layer and an outer exposure layer with a gap volume between the inner and outer layers, and transferring the phase changing material to the gap volume between the inner and outer layers of the enclosure structure.

In optional variations, the phase changing material can include one or more of organic materials such as wax and fatty acid, inorganic materials such as hydrate salts, and eutectic materials. The phase change materials can be encapsulated in a membrane or otherwise contained within some kind of barrier. The enclosure can further include an inner shell disposed within the outer shell such that a gap volume exists between the outer shell and the inner shell. The one or more gas analyzer components can be disposed within the inner shell, and the mass of phase changing material can be disposed within the gap volume.

More than one phase change material, each having a different target temperature can be used to provide additional temperature stability, over a wider temperature range. The first and the second phase changing materials can be disposed in an arrangement in which the first phase changing material is disposed in a first layer closer to the outer shell of the enclosure and the second phase changing material is disposed in a second layer closer to the one or more gas analyzer components. Alternately, the first and second phase changing materials can be randomly mixed. The enclosure can include a heater and/or a cooler unit as well as a temperature sensor and/or a temperature controller circuit or subroutine that provides back-up temperature control in the event that the latent heat associated with phase changes of the phase change material is not sufficient to stabilize the temperature of the analyzer contained within the enclosure at a preferred temperature. The heater or cooler device can be activated by the controller if the signals from the temperature sensor indicate that an internal temperature inside the enclosure has deviated by more than a threshold amount form the phase transition temperature of the phase changing material. An additional mass of the phase changing material can be included to absorb heat generated within the enclosure by the one or more gas analyzer components. The one or more gas analyzer components can include one or more of a tunable diode laser head, a detector, and a sample cell.

A processor can be included that receives signals from the detector and that controls the tunable diode laser to produce light within a wavelength range, the light being directed into the sample cell to pass through a gas sample contained within the sample cell and to be received at the detector after passing through the gas sample, the detector quantifying an intensity of the light received after passing through the gas sample, the signals received by the processor from the detector containing data on the intensity, the processor calculating a concentration of at least one target analyte in the gas sample based on the signals.

Various implementations and/or aspects of the subject matter described herein can provide one or more advantages or benefits, potentially including but not limited to the following. The use of phase changing materials (PCM) as insulation for tunable diode laser (TDL) gas analyzers can passively improve laser frequency stability and accuracy, with regard to one or more chosen trace gas absorption lines. Improved temperature and frequency stability of the spectrometer cell, laser source, and/or other components translates directly into enhanced sensitivity, measurement stability, and accuracy. Using PCM materials can minimize energy consumption of TDL and other trace gas analyzer systems by either eliminating the need for expensive, energy consuming heating and/or cooling systems or at least reducing the power load required by such systems. Heater systems for TDL trace gas analyzers can be especially expensive when hazardous location certification such as CSA, ATEX or IECEx is required for the analyzer. PCM-based systems and methods such as those disclosed herein can also be highly reliable and intrinsically safe for example because there are no mechanical or electrical parts in the PCM. Passive operational safety can be an important consideration for hazardous location certification, which is a must for all trace gas analyzers used on NG pipe lines and in petrochemical plants. Additionally, little or no maintenance is typically necessary.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed embodiments. In the drawings.

DETAILED DESCRIPTION

The currently disclosed subject provides methods, systems, techniques, apparatuses, and article of manufacture for maintaining a stable temperature for an analyzer, such as for example a gas analyzer based on a tunable diode laser. A mass of phase changing material (PCM) is incorporated into the design of an enclosure for the analyzer. This PCM mass provides thermal buffering at a phase transition temperature due to the latent heat that is absorbed as the PCM transitions to a more entropic state (i.e. gas or liquid) or released as the PCM transitions to a less entropic state (i.e. liquid or solid). Because the phase change takes place at a fixed phase transition temperature with large latent heat buffering heat exchange from ambient, the analyzer components inside the enclose are isolated from variations in the ambient temperature to which the enclosure is exposed. This will help to guarantee the accuracy and repeatability of the analyzer readings. The subject matter described herein can improve the feasibility of maintaining analytical equipment at a temperature at or below the maximum ambient temperature experienced at the installation point of the analytical equipment. The thermal buffering capacity of the PCM can be recharged during cooler periods of time, such as for example overnight. One or more cooling devices and/or temperature monitoring equipment and a controller could also be installed in the enclosure to assist in maintaining the internal temperature at the desired value. In many commercially available analytical equipment enclosures, a constant temperature is typically maintained by heating the internal volume of the enclosure to a temperature exceeding that likely to be experienced in the ambient environment and then adding heat to the interior as necessary to compensate for net heat outflows and thereby maintain a constant or near constant temperature. This procedure can be expensive from an energy standpoint as noted above and can also limit the available temperature range at which the analytical equipment can be operated.

The term "phase changing materials" generally refers to materials that change their physical phase at a phase transition temperature. In the current disclosure, PCM refers to materials having a phase transition temperature near a desired operating temperature of a system. During a phase transition both phases of the PCM co-exist. The physical phase change can be between the liquid and solid phases, the liquid and gas phases, or even the solid and gas phases (sublimation). All or nearly all materials undergo such phase changes if subjected to heat input or output at the phase transition temperature (i.e. freezing, boiling, or sublimation point). As the PCM changes phase, it absorbs (or releases) latent heat at a single, phase transition temperature that is maintained as long as both phases of the PCM are present.

As an example, a system that includes distilled water containing ice cubes will stay at exactly 0° C. until enough heat is absorbed by the system to melt all of the ice or, alternatively, until enough heat escapes from the system to cause all of the liquid water to freeze. Once either condition occurs, the temperature of the system can begin to deviate from 0° C. The PCM takes up heat when it transforms from solid to liquid and gives off heat again when it solidifies. In this manner, a PCM can mitigate temperature changes and maintain constant temperature over an ambient temperature range defined by the total amount of heat required to cause 100% phase change for a given mass of the PCM. According to the current subject matter, a properly selected PCM can maintain the temperate of a gas analyzer system or apparatus at or near a stable value while the system or apparatus undergoes a net positive or net negative heat exchange with the environment or some other heat source or sink, such as for example internal heat generation.

Available PCMs include but are not limited to organic materials such as wax and fatty acid, inorganic materials such as hydrate salts, and eutectics. Examples of organic PCMs—include but are not limited to paraffin (i.e. $C_nH_{2n+2}$) and fatty acids (i.e. $CH_3(CH_2)_{2n}COOH$). Inorganic PCMs can include but are not limited to salt hydrates (i.e. $M_nH_2O$). Eutectic PCM systems can include mixtures of materials, such as for example organic-organic, organic-inorganic, and inorganic-inorganic compounds. Organic materials generally are available in a large range of phase transition temperatures, freeze without a great degree of supercooling, tend to melt congruently and have self-nucleating properties, and are chemically stable. However, their volumetric latent heat storage capacity can be relatively low, and they tend to be flammable or combustible. Inorganic materials generally have a high volumetric heat storage capacity, low cost and easy availability, and are non-combustible. However, supercooling can present problems in the transition from solid to liquid, and nucleating agents may be needed to encourage phase change at the transition temperature without hysteresis. Eutectic materials can be non-combustible if they are based on inorganic materials. Other data on the thermo-physical behavior of these materials is scarce as they are relatively new. Encapsulation of the PCM is optional according to the current subject matter. In some designs, PCM can be used in a sealed system that allows sufficient space for changes in density of the PCM during the phase change process. In some implementations of the current subject matter, particles of $C_{18}H_{38}$ can be used as the PCM. The particles can be used in an encapsulated configuration as described below.

For example, a system containing liquid and solid water (ice) will remain at or near 0° C. despite a net flow of energy into or out of the system until all of the ice has melted or all of the liquid water has frozen. Only after the latent heat of phase change has been absorbed or released does the temperature of the system begin to deviate from the phase change temperature. For a given mass of PCM to maintain a stable temperature for a given period of time, the latent heat of the PCM material must be greater than or equal to the net heat input to or withdrawal from the system during the period. This net heat input or withdrawal form the system can be due to thermal exchange with the ambient environment or due to heat sinks or sources within the enclosure or otherwise associated with the analytical equipment or the gases being sampled. Expressed mathematically, $$\rho \cdot c \cdot V \geq h \cdot A \cdot t \cdot \Delta T \qquad (2)$$

where $\rho$ is the density of the PCM ($kg \cdot m^{-3}$), which can be approximately $0.9 \times 10^3 \cdot kg^{-1} \cdot m^{-3}$ in some examples; c is the latent heat of the PCM $kJ \cdot kg^{-1}$, which can be approximately 180 $kJ \cdot kg^{-1}$ in some examples; V is the volume of the PCM ($m^3$); h is the heat transfer coefficient of the system ($W \cdot m^{-2} \cdot K^{-1}$), which for natural convection in air is approximately 5 $W \cdot m^{-2} \cdot K^{-1}$; A is the surface area over which heat dissipation occurs ($m^2$); t is the time duration of the period of heat input or withdrawal (h), which can be approximately 12 h over the course of a day; and $\Delta T$ is the average temperature difference (K), which can be approximately 20 K for an ambient temperature range of approximately −20° C. to 60° C.

For a cubic structure of edge length L made entirely of PCM, the volume of PCM is given by $$V = L^3 \qquad (3)$$

and the cross section area, A, is $$A = 6 \cdot L^2 \qquad (4).$$

Therefore, the minimum value of L for the cube to remain at a constant temperature given the parameters discussed above is $$L \geq \frac{6 \cdot h \cdot t \cdot \Delta T}{\rho \cdot c} = \frac{6 \cdot (5 \ W \cdot m^{-2} \cdot K^{-1})(12 \ h \times 3600 \ s \cdot h^{-1})(20 \ K)}{(900 \ kg \cdot m^{-3})(180 \ kJ \cdot kg^{-1} \times 1000 \ J \cdot kg^{-1})} = 0.16 \ m \qquad (5)$$

which corresponds to a cubic volume of greater than or equal to 0.0041 $m^3$ and a PCM mass of 3.7 kg or about 8.1 pounds assuming a PCM density of 900 $kg \cdot m^{-3}$.

The presence of the PCM in a buffer layer positioned between the gas analyzer components and the external environment can help to maintain the gas analyzer at a stable temperature. Because phase change takes place at a fixed temperature with large latent heat buffering heat exchange from ambient, the analyzer components inside the enclosure can be minimally affected by the ambient temperature variations. Because outdoor temperature typically follows a diurnal cycle, a properly selected PCM with a sufficient mass and a phase transition temperature that lies within the expected range of ambient temperatures can act as a sort of "rechargeable" thermal buffer. For example, during daylight hours when the thermal flux from the environment is likely to be net positive, a net change from the condensed phase (i.e. solid or liquid) to the more entropic phase (i.e. liquid or gas) of the PCM occurs. At night when the ambient temperature is generally cooler, the net thermal flux would be from the analyzer back to the environment. A net change of the PCM from the more entropic to the more condensed phase should occur during this time. When the next daylight cycle begins, the cycle resumes.

Figure 1:
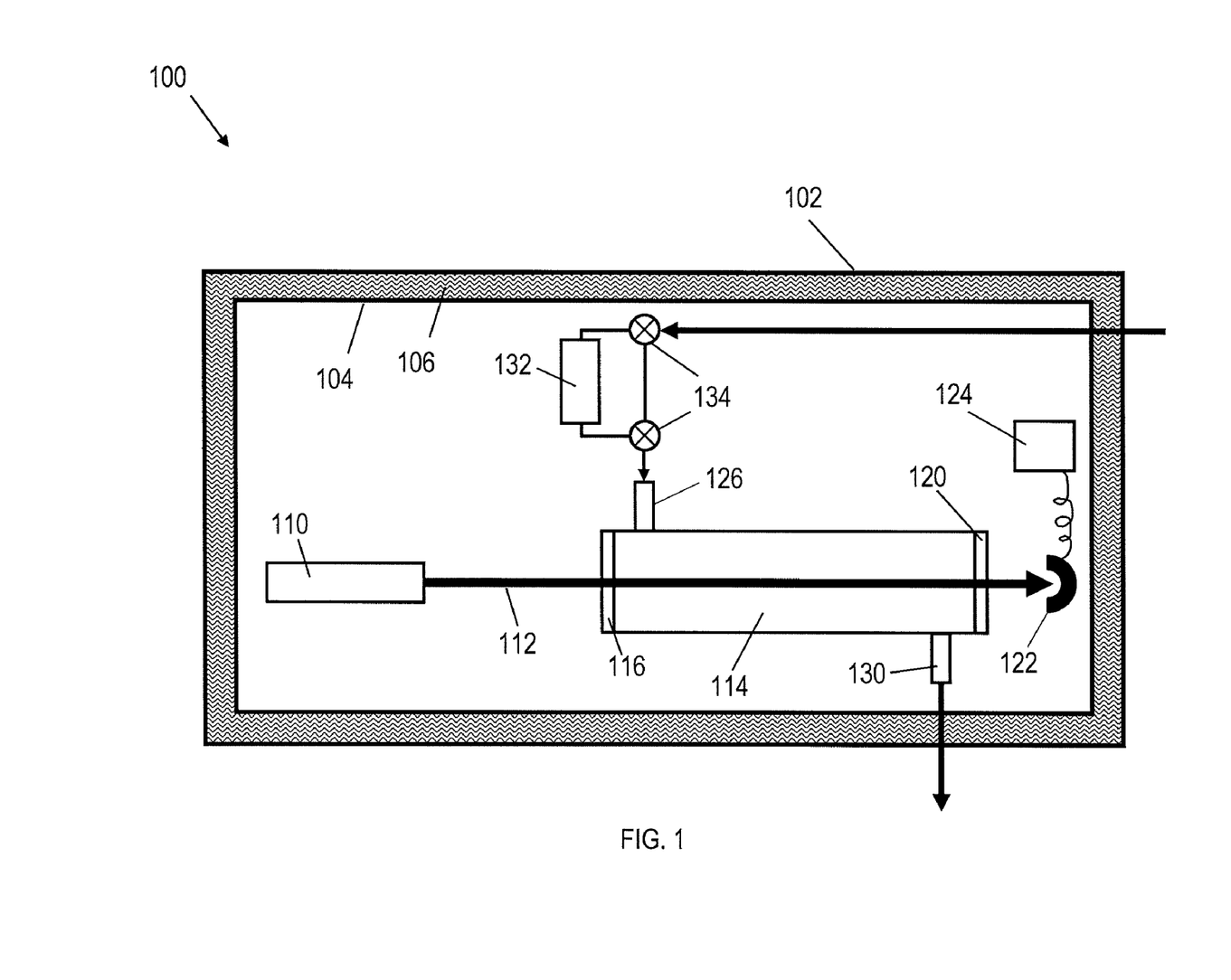
FIG. 1 is a schematic diagram showing a gas analyzer with an enclosure featuring a phase changing material.

In one implementation, a phase-changing material is incorporated into a gas analyzer enclosure 100 using a double-walled enclosure design as shown in FIG. 1. An outer enclosure layer 102 defines the dimensions and appearance of the gas analyzer, and can include one or more features for example for securing the analyzer to a support. This outer layer 102 can have explosion resistant properties if flammability or hazardous material exposure is a concern in a specific installation of the gas analyzer. An internal enclosure layer 104 separates a layer of PCM 106 from components of the analyzer, for example to maintain clear access for maintenance, etc. The components of the gas analyzer can in some examples include a light source 110 that produces light in a beam or pulses 112 that passes through one or more sample cells 114, possibly via a first window 116 and then out through a second window 120 to a photodetector 122 that provides data to a processor 124. Gas can flow into the sample cell 114 via an inlet 126 and out through an outlet 130.

In an example in which the gas analyzer is used for differential absorption spectrometry, the gas analyzer can include a scrubber 132 or other device for reducing the concentration of one or more components of the gas mixture to be analyzed. One or more valves or other tubing and/or gas routing components 134 can be provided, for example to alternately provide gas to the one or more sample cells 114 either directly or via the scrubber 132. Multiple sample cell arrangements can also be used in which the scrubber 132 is connected in series with a first sample cell while a second sample cell receives unscrubbed gas and wherein the light source 110 is split between the sample cells. If the sample cells have substantially similar path lengths, both spectra for use in the differential absorption analysis can be collected in parallel. An enclosure as described herein can also house gas analyzers that are used for direct absorption spectroscopy, as well as numerous other applications. In one possible variation, an analyzer system with two or more sample cells can be deployed with one or more sample cells thermally buffered with PCM as described above, and one or more sample cells exposed to ambient conditions. Such an arrangement could be used in ambient gas analyses or other applications in which it is desirable to maintain the sampled gas at its original temperature and pressure.

Figure 2:
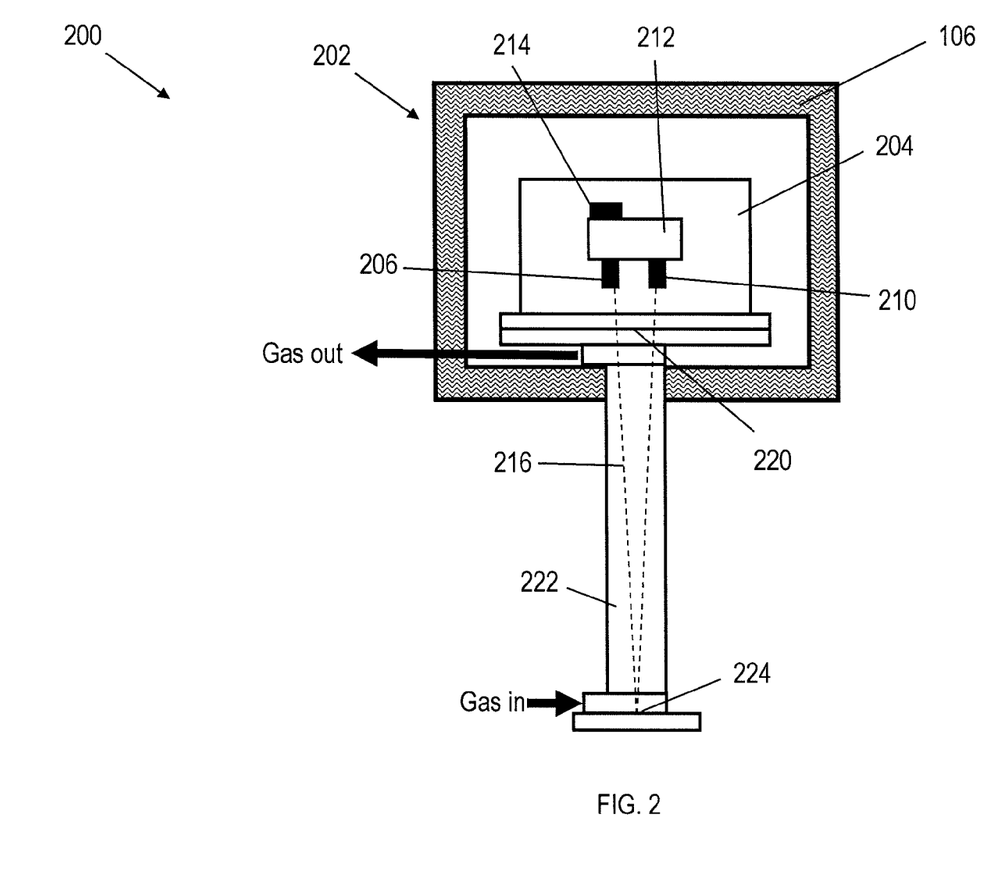
FIG. 2 is a schematic diagram showing a gas analyzer with an enclosure featuring a phase changing material that encloses the optical head of the analyzer.

In an alternative implementation, an example of which is shown in the system 200, PCM can be incorporated into an enclosure 202 that houses only some of the gas analyzer components, such as for example an optical head 204 that includes the light source 206 and the photodetector 210. As in FIG. 12, the enclosure 202 includes outer enclosure layer 102 that defines the dimensions and appearance of the gas analyzer and an internal enclosure layer 104 that separates a layer of PCM 106 from the encased components, in this example the optical head 204. The optical head 204 can further include a baseplate 212 whose temperature is controlled by a thermoelectric cooler (TEC) 214. The light source 206, for example a laser such as a tunable diode laser, and the photodetector 210 can be mounted to the baseplate 212 for better thermal control. In this example, the light 216 generated by the light source 206 is directed out of the optical head 204 through a window 220 into a sample cell 222 that contains a sample of the gas to be analyzed. As shown in FIG. 2, the light 216 travels the length of the sample cell 222 twice as it is reflected at the far end of the sample cell 222 by a flat mirror 224. The returning light is transmitted back through the window 220 and impinges on the photodetector 210. Gas can pass into and out of the sample cell 222 via ports as shown in FIG. 2.

For an enclosure that surrounds only a sealed optical head 204, the inner enclosure layer 104 can optionally be omitted such that the sealed exterior of the optical head 204 forms a barrier that maintains the PCM in its proper position. As noted above in the example of FIG. 1, the PCM can be separately encapsulated, for example in flexible sealed bags or rigid or semi-rigid sealed containers to avoid leakage of the PCM or other problems such as corrosion or contamination that could arise from allowing a liquid material to come into contact with components of the analyzer 200. An estimation of the mass of PCM required for this example can be obtained by assuming a cube-shaped mass of PCM having a side length of L that encases an optical head volume of $V_{head}$. The cross-sectional area that the sample cell 222 occludes is given by $A_{cell}$. For simplicity, heat transfer across this area is assumed to be zero, and the optical head 204 is assumed to have a cube shape with a side length of $L_{head}$. With this assumption and the further assumption that the cross section area of the cell ($A_{cell}$) is the same as the area of a side of the cube-shaped optical head 204, the optical head volume is given by $V_{head}=L_{head}^3$ and the heat transfer area occluded by the sample cell 222 is given by $A_{cell}=L_{head}^2$. Substituting into equation 1 gives:

$$\rho \cdot c \cdot (L^3 - L_{head}^3) \leq h \cdot (6 \cdot L^2 - L_{head}^2) \cdot t \cdot \Delta T \quad (6)$$

For a sample cell 222 with a cross sectional area of about 10 cm² (0.1 m on a side) and using the values used above in equation 5, $$\rho \cdot c \cdot L^3 - 6 \cdot h \cdot t \cdot \Delta T \cdot L^2 = \rho \cdot c \cdot L_{head}^3 - h \cdot t \cdot \Delta T \cdot L_{head}^2 \quad (7)$$

which produces a cubic equation that can be solved for L to give a value of approximately 0.18 m or 18 cm. Using this value, the total volume of the cube-shaped enclosure would be 0.006 m³ or about 6000 cm³. The total volume of PCM needed is this volume minus the volume of the optical head 204, which is 0.001 m³ or about 1000 cm³. The total PCM mass needed would therefore be approximately 4.5 kg or 9.9 pounds assuming a PCM density of 900 kg·m³. It should be noted in this example that internal heat loads, such as heat that might be convected into the sample cell via the gas being sample or heat generation by electronic circuitry, the laser light source, or the like are not considered. Such heat loads can typically be assumed to be relatively constant.

Figure 3:
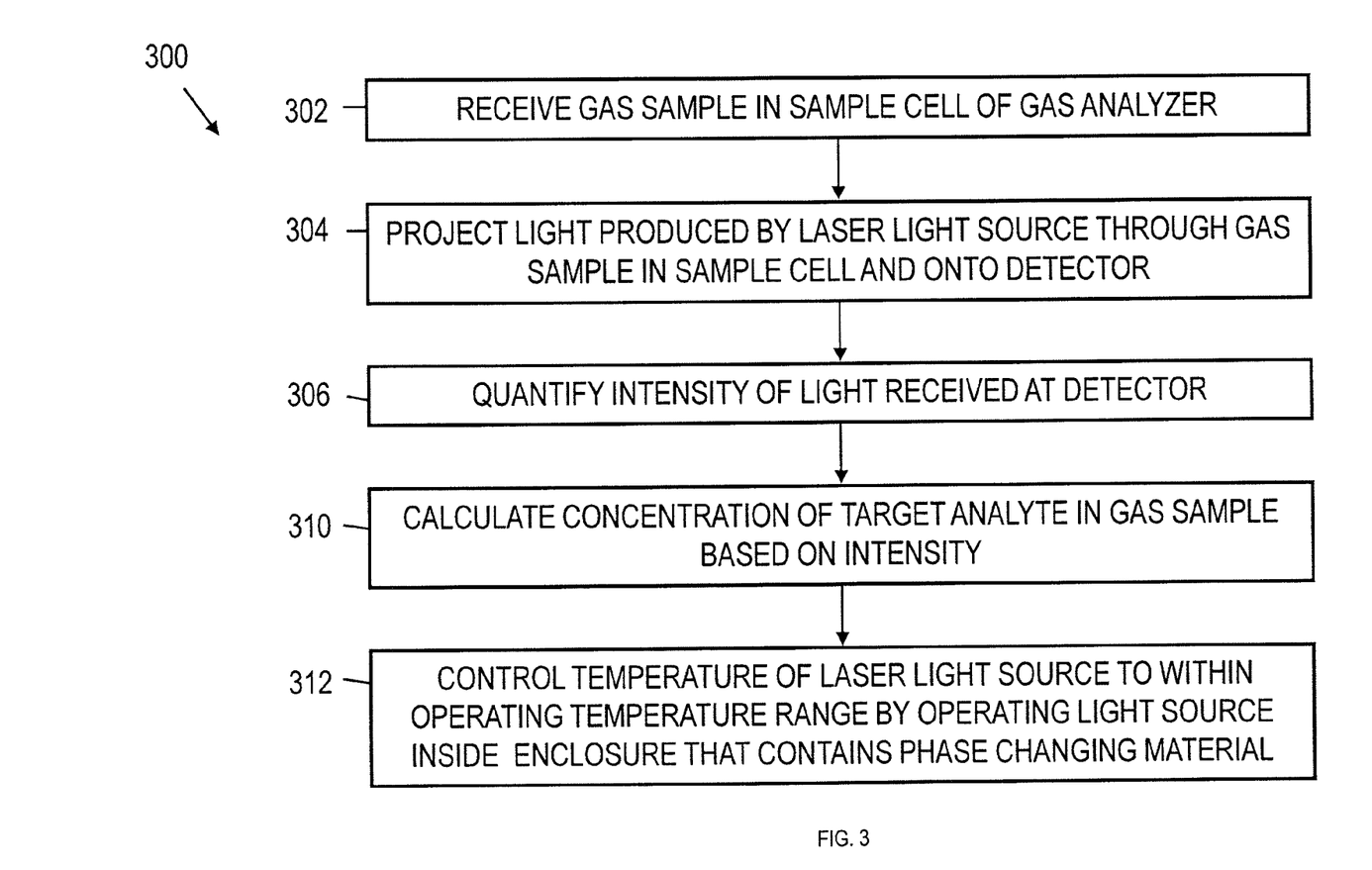
FIG. 3 is a process flow diagram illustrating a method for determining a target analyte concentration in a gas sample.

In a further implementation, a concentration of a target analyte in a gas sample can be determined according to a method 300 as shown in FIG. 3. At 302, a sample cell of a gas analyzer receives a gas sample that contains a target analyte. At 304, a laser light source generates light that is projected through the gas sample in the sample cell and onto a detector. An intensity of the light received at the detector is quantified at 306, and at 310 a concentration of at least one target analyte in the gas sample based is calculated on the intensity. At 312, the temperature of the laser light source is controlled to within an operating temperature range by operating the light source inside of an enclosure that comprises an outer shell that is resistant to and compatible with an operating environment. The outer shell contains a mass of a phase changing material that has a phase transition temperature at which the phase changing material transitions from a first phase to a second phase while absorbing or releasing a latent heat energy $\Delta H_L$. The phase transition temperature is within the operating temperature range. The mass M of the phase changing material is given by equation 1 based on $\Delta H_L$ and the net heat flux into the enclosure $F_T$.

Additional mass of the PCM can also be included if one or more of the gas analyzer components is expected to be a substantial source of heat. In this example, the PCM must have sufficient latent heat capacity to absorb both the net heat flux into the enclosure $F_T$ as discussed above and the heat generated by the components within the enclosure $H_C$. In operating environments that experience a substantial temperature range over the course of a day, for example very cold at night relative to daytime temperatures, it may be possible to operate such a system without additional heating or cooling devices. For thermal equilibrium to be maintained over daily cycle, the net heat flux out of the enclosure during periods of lower ambient temperature (i.e. overnight), $F_{T,out}$, should be approximately equal to the amount of heat generated in the enclosure by the analyzer components ($H_C$) plus the net heat flux into the enclosure during periods of higher temperature ($F_T$). Mathematically, $$F_{T,Out} \approx F_T + H_C \quad (8).$$

The magnitude of $H_C$ can be changed by the use of, for example, a cooling device such as a thermoelectric cooler within the enclosure or by using a heat pump or external heat sink to dissipate internally generated heat to the exterior of the enclosure. The use of PCM as discussed herein serves as a thermal buffer to absorb excess heat during high positive thermal flux periods and to retain heat during high negative thermal flux periods.

Figure 4:
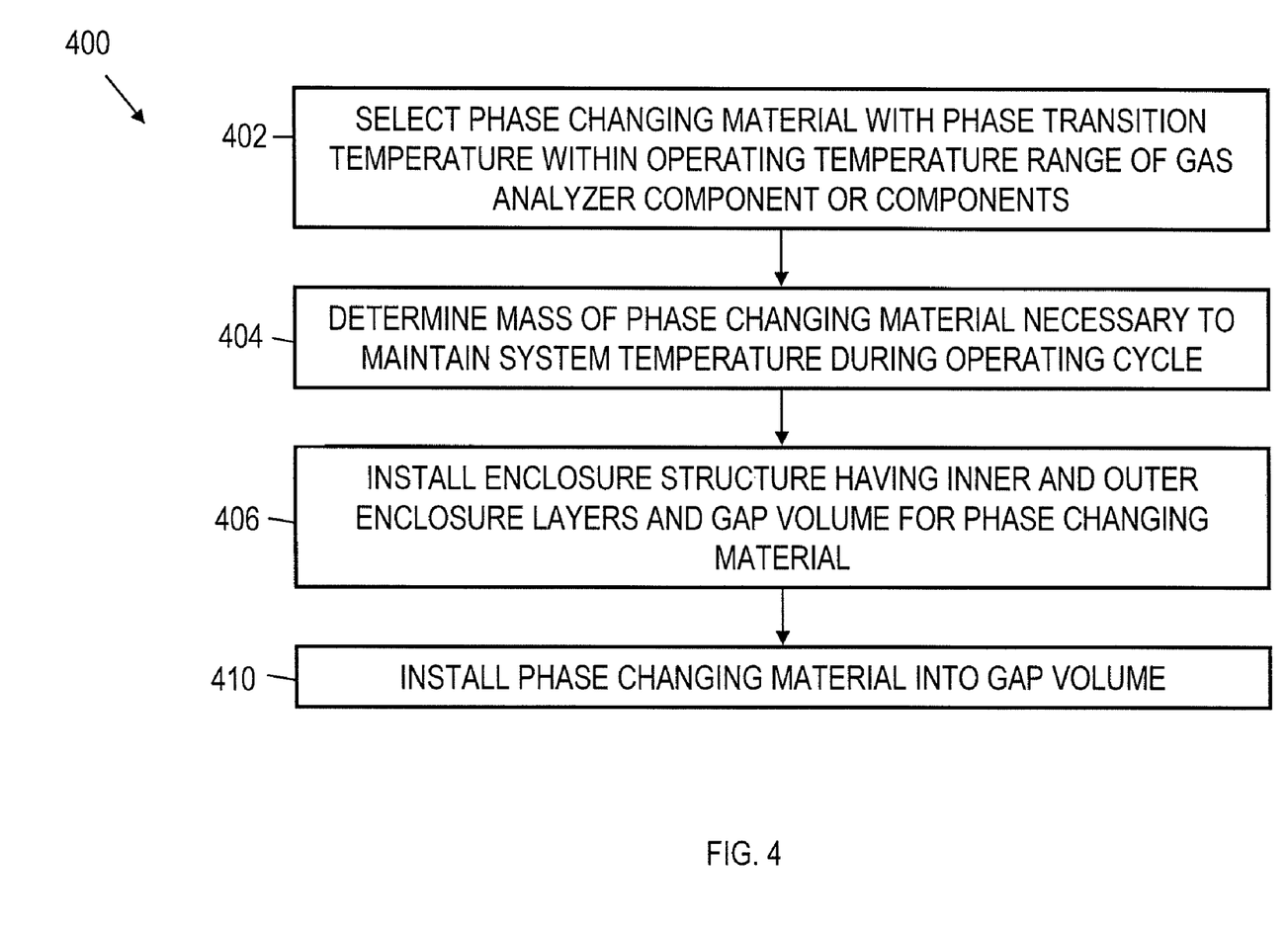
FIG. 4 is a process flow diagram illustrating a method for producing a gas analyzer incorporating phase changing materials.

In another implementation, a gas analyzer enclosure can be prepared according to a method 400 as shown in FIG. 4. At 402, a phase changing material is selected such that the phase transition temperature of the phase changing material is within an operating temperature range of one or more components of a gas analyzer. One or more phase changing materials can be selected based on the operating temperature range and the expected ambient temperature conditions to which the gas analyzer is expected to be exposed. The mass of phase changing materials necessary to maintain the gas analyzer system or individual components at the desired constant temperature is calculated at 404 using equation 1. This calculation can be based on estimates of one or more of the heat transfer rate from the environment in which the gas analyzer is to be operated, the rate of internal heat generation in the gas analyzer (for example due to operation of pumps, the laser source, the detector, one or more electronics subsystems, or the like), and the time duration of the temperature cycle to which the gas analyzer is anticipated to be exposed. Heat transfer from the ambient environment can typically be through one or more of natural convection, conduction, and radiative heat transfer. The time duration of exposure in a temperature cycle can in some examples be assumed to be half of a day or 12 hours.

At 406, an enclosure structure is installed including an inner enclosure layer and an outer exposure layer with a gap between the inner and outer layers for positioning of the PCM. The gap between the inner and the outer layers advantageously includes a sufficient gap volume to contain the full mass of PCM determined at 404. At least one opening can optionally be provided to allow PCM to be placed within the gap after assembly of the inner and outer layers into the enclosure structure. The volume encompassed by the inner layer of the enclosure is advantageously large enough to house all of the temperature sensitive components of the gas analyzer. At 410, the PCM is transferred to the gap volume between the inner and outer layers of the enclosure structure. The PCM can optionally be encapsulated in one or more flexible or rigid substructures so as to retain the PCM within the gap volume where tubing and/or other pass-through devices or features are necessary for the gas analyzer components to communicate with the exterior of the enclosure structure.

In some implementations, two or more phase changing materials with different phase transition temperatures can be incorporated into a single enclosure. In one example, each individual PCM can be segregated into one or more sealed sub-enclosures to avoid colligative effects on the phase transition temperature that might arise from mixing two materials with different properties. In one possible variation, a first layer of a first PCM having a first phase transition temperature is disposed closer to the outer shell of the enclosure and a second layer of a second PCM having a second phase transition temperature is disposed inward of the first layer of PCM and closer to the one or more gas analyzer components. The first phase transition temperature can be lower than the second phase transition temperature so that as the apparatus is exposed to a net positive flux of heat into the enclosure from the ambient environment, the first PCM buffers the temperature at the first phase transition temperature and the second PCM layer remains in the lower entropy (i.e. solid) state. When the first PCM layer has completely transitioned to the higher entropy state due to absorbing sufficient heat from the ambient environment to overcome its latent heat capacity, the temperature of the first PCM layer can rise. As the first PCM layer temperature reaches the second phase transition temperature, the second PCM layer begins to transition from lower entropy state to higher entropy state while absorbing additional latent heat energy that does not cause the gas analyzer components housed within the second PCM layer to increase in temperature above the second phase transition temperature.

Phase changing materials could also be included in a gas analyzer design in which PCM are placed on the "hot" side of a thermoelectric cooler (TEC) to absorb waste heat generated when the TEC cools a semiconductor laser to its required temperature.

EXAMPLE

Figure 5:
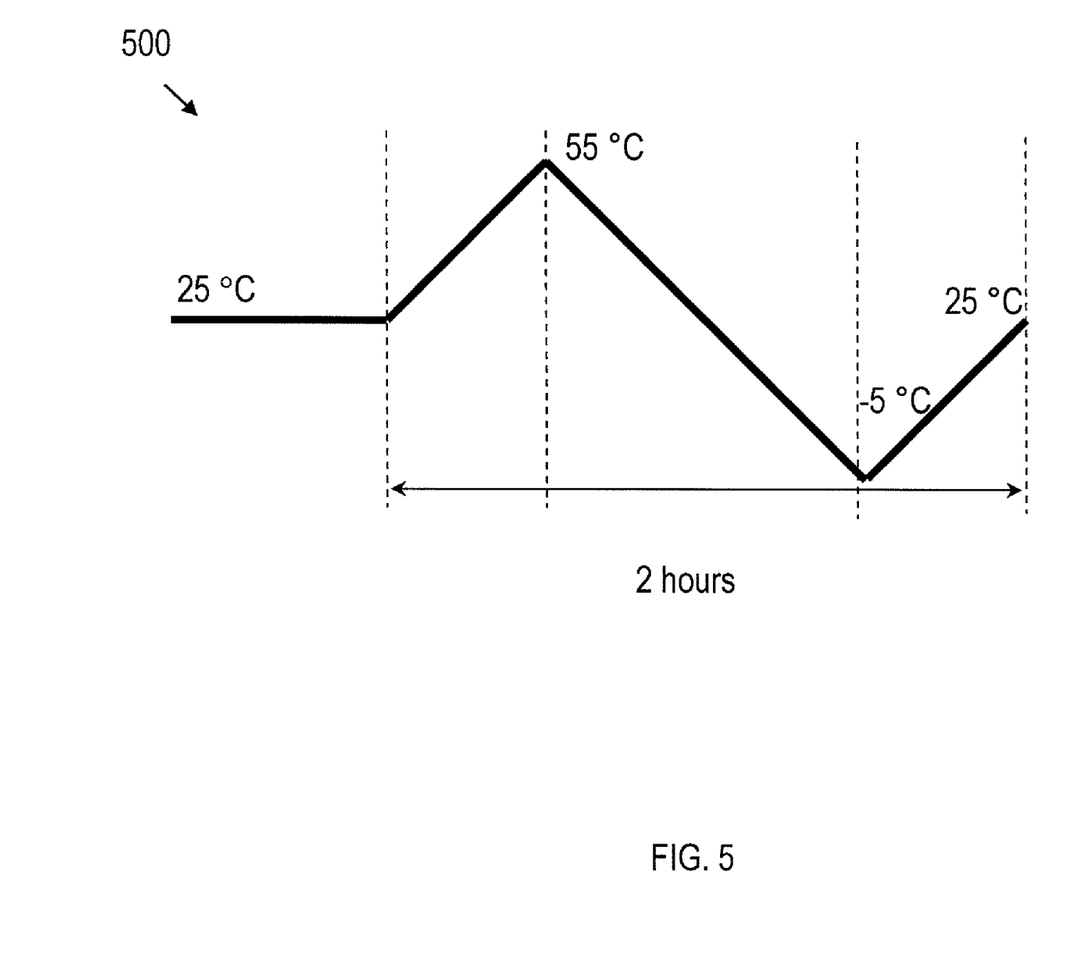
FIG. 5 is a chart showing the temperature ramp profile for a demonstration of the performance of an enclosure according to the current subject matter.
Figure 6:
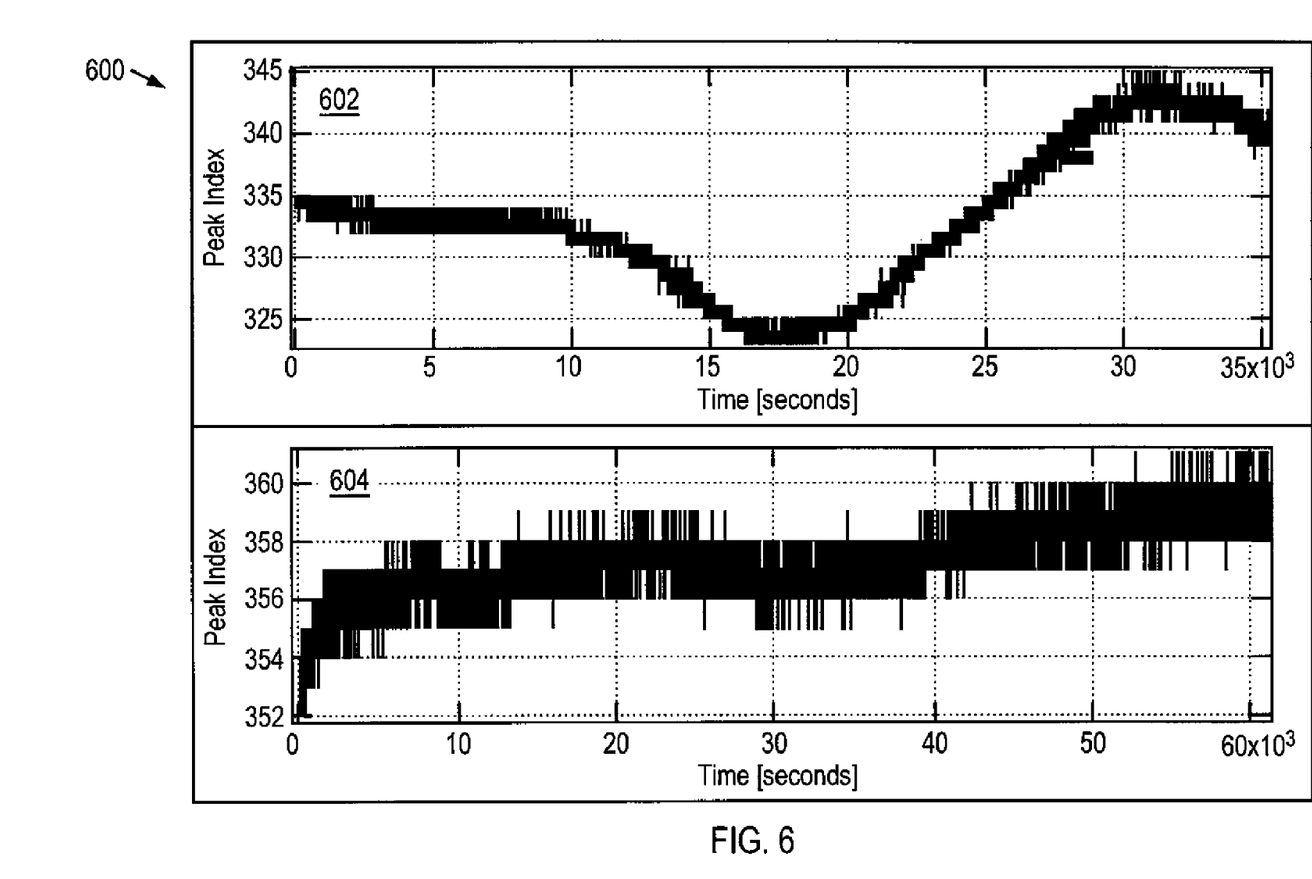
FIG. 6 shows two charts illustrating a possible beneficial effect of using PCM in a gas analyzer enclosure.

In an illustrative example of the use of PCM with a gas analyzer in accordance with the current subject matter, it is desirable to minimize the laser peak index shift for a tunable diode laser to less than 5 counts after the laser is fully warmed up an operational. The laser peak index shift is a direct indication of the laser's frequency shift. In this example, the laser generates 16 counts per mA injection current. The analyzer used in these calculations employs a 28 m cell with a 1590 nm laser such as that available from SpectraSensors, Inc. (Rancho Cucamonga) in a model 2100 $H_2S$ analyzer. The gas analyzer was operated over a range of temperatures according to the temperature ramp profile 500 shown in FIG. 5. The rate of temperature change between temperature set points was 1° C. between a starting and ending temperature of 25° C. with intermediate temperatures of 55° C. and −5° C. As a baseline, the peak index was monitored for the laser operating both without and with a PCM enclosure according to the current subject matter. The PCM used in this example was 10 lbs of encapsulated $C_{18}H_{38}$ particles. The results of this demonstration are shown in the chart 600 of FIG. 5 which shows the results for the non-PCM run in 602 and the with-PCM run in 604. As shown in 502, the peak index shifts by 10 counts or more above and below the baseline of 335 during the temperature profile shown in FIG. 5. In contrast, the peak index is much more stable, even for two hours after the end of the temperature ramp profile in 604.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts. Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein do not require the particular order shown, or sequential order, to achieve desirable results. Other embodiments may be within the scope of the following claim.

What is claimed is:

1. An apparatus comprising
    an enclosure comprising an outer shell that is resistant to and compatible with an operating environment and an inner shell disposed within the outer shell such that a gap volume exists between the outer shell and the inner shell;
    one or more gas analyzer components disposed within the inner shell; and
    a mass of a phase changing material disposed within the gap volume between the outer shell and the inner shell, the phase changing material having a phase transition temperature at which the phase changing material transitions from a first phase to a second phase while absorbing or releasing a latent heat energy $\Delta H_L$, the phase transition temperature being within a desired operating temperature range of the one or more gas analyzer components, the mass M of the phase changing material being given by $$M \geq \frac{F_T}{\Delta H_L}$$

where $F_T$ is an expected net heat energy flux from the operating environment into the enclosure during a period of an operating day during which an ambient temperature outside of the enclosure exceeds the phase transition temperature.

2. An apparatus as in claim 1, wherein the one or more gas analyzer components comprise one or more of a tunable diode laser, a detector, and a sample cell.

3. An apparatus as in claim 2, further comprising a processor that receives signals from the detector and that controls the tunable diode laser to produce light within a wavelength range, the light being directed into the sample cell to pass through a gas sample contained within the sample cell and to be received at the detector after passing through the gas sample, the detector quantifying an intensity of the light received after passing through the gas sample, the signals received by the processor from the detector containing data on the intensity, the processor calculating a concentration of at least one target analyte in the gas sample based on the signals.

4. An apparatus as in claim 1, further comprising an additional mass of the phase changing material, the additional mass being sufficient to absorb heat generated within the enclosure by the one or more gas analyzer components.

5. An apparatus as in claim 1, wherein the phase changing material comprises one or more of a wax, a fatty acid, a hydrate salt, and a eutectic material.

6. An apparatus as in claim 1, wherein the phase changing material is $CH_3(CH_2)_{2n}COOH)$.

7. An apparatus as in claim 1, wherein the phase changing material is $C_nH_{2n+2}$.

8. An apparatus as in claim 1 wherein the phase changing material is $M_nH_2O$.

9. An apparatus as in claim 1, further comprising a sealed enclosure that contains the phase changing material.

10. An apparatus as in claim 1, further comprising at least one second mass of a second phase changing material having a second phase transition temperature that differs from the phase transition temperature, the second mass of the second phase changing material being disposed in a second layer outward of a first layer of the mass of the phase changing material and closer to the outer shell of the enclosure, the second phase changing material having a second phase transition temperature that is lower than the phase transition temperature of the phase changing material in the first layer.

11. An apparatus as in claim 1, further comprising a temperature sensor disposed within the outer layer of the enclosure, one or more of a heating device and a cooling device, and a controller that receives signals from the temperature sensor and controls the one or more of the heating device and the cooling device to provide back-up temperature control if the signals from the temperature sensor indicate that an internal temperature inside the enclosure has deviated by more than a threshold amount from the phase transition temperature of the phase changing material.

12. A method comprising:
receiving a gas sample in a sample cell of a gas analyzer;
projecting light produced by a laser light source through the gas sample in the sample cell and onto a detector;
quantifying an intensity of the light received at the detector;
calculating a concentration of at least one target analyte in the gas sample based on the intensity;
controlling a temperature of the laser light source to within an operating temperature range, the controlling comprising operating the light source inside of an enclosure that comprises an outer shell that is resistant to and compatible with an operating environment, the outer shell containing a mass of a phase changing material incorporated into the design of the outer shell and acting as a buffer layer positioned between the gas analyzer components and the operating environment, the phase changing material having a phase transition temperature at which the phase changing material transitions from a first phase to a second phase while absorbing or releasing a latent heat energy $\Delta H_L$, the phase transition temperature being within the operating temperature range, the mass M of the phase changing material being given by $$M \geq \frac{F_T}{\Delta H_L}$$

where $F_T$ is an expected net heat energy flux from the operating environment into the enclosure during a period of an operating day during which an ambient temperature outside of the enclosure exceeds the phase transition temperature.

13. A method as in claim 12, wherein in addition to the laser light source the enclosure houses one or more of the sample cell and the detector.

14. A method as in claim 12, wherein the calculating of the concentration of the at least one target analyte in the gas sample based on the intensity is performed by a processor that receives signals from the detector and that controls the laser light source.

15. A method as in claim 12, wherein the controlling further comprises monitoring an internal temperature within the enclosure and operating a heating or cooling device within the enclosure if the internal temperature deviates outside of the operating temperature range.

16. A method comprising:
selecting a phase changing material having a phase transition temperature at which the phase changing material transitions from a first phase to a second phase while absorbing or releasing a latent heat energy $\Delta H_L$, the phase transition temperature being within an operating temperature range of one or more gas analyzer components, the one or more gas analyzing components comprising a laser light source;
calculating a necessary mass M of the phase changing material necessary to maintain the one or more gas analyzer components with the operating temperature range, wherein $$M \geq \frac{F_T}{\Delta H_L}$$

where $F_T$ is an expected net heat energy flux from an operating environment into an enclosure housing the one or more gas analyzer components and the phase changing material, the net heat energy flux occurring during a period of an operating day during which an ambient temperature outside of the enclosure exceeds the phase transition temperature;

assembling the enclosure, the enclosure comprising an inner enclosure layer and an outer exposure layer with a gap volume between the inner and outer layers; and transferring the phase changing material to the gap volume between the inner and outer layers of the enclosure structure.

17. A method as in claim 16, wherein the enclosure comprises at least one opening through which the phase changing material is placed within the gap volume after assembly of enclosure.

18. A method as in claim 16, wherein the phase changing materials are encapsulated in one or more flexible or rigid substructures to retain the phase changing materials within the gap volume and to prevent leakage of the phase changing material in a fluid phase out of the gap volume where tubing and/or other pass-through devices or features of the one or more gas analyzer components penetrate the gap volume.

19. A method as in claim 16, wherein the calculating of the necessary mass further comprises estimating one or more of the heat transfer rate from the environment in which the gas analyzer is to be operated, the rate of internal heat generation in the gas analyzer, and the time duration of the temperature cycle to which the gas analyzer is anticipated to be exposed.

20. A method as in claim 16, further comprising installing a controllable heat source or sink within the enclosure to provide or remove additional heat if the laser light source experiences a temperature outside of the operating temperature range.

21. The apparatus of claim 1, wherein the mass of the phase changing material in full is confined to the gap volume between the inner shell and outer shell, and further wherein the gap volume comprises sufficient space for changes in density of the phase changing material during a phase change.

* * * * *